United States Patent [19]

Taylor et al.

[11] Patent Number: 5,601,551

[45] Date of Patent: Feb. 11, 1997

[54] GEARED EXTERNAL FIXATOR

[75] Inventors: Harold S. Taylor; J. Charles Taylor, both of Memphis, Tenn.

[73] Assignee: Smith & Nephew Richards, Inc., Memphis, Tenn.

[21] Appl. No.: 396,925

[22] Filed: Mar. 1, 1995

[51] Int. Cl.$^6$ ................................................ A61B 17/56
[52] U.S. Cl. ........................... 606/54; 606/57; 606/58; 606/53
[58] Field of Search ...................... 606/53, 54, 55, 606/56, 57, 58, 59, 105; 74/89.14, 424.6

[56] References Cited

U.S. PATENT DOCUMENTS

| | | | |
|---|---|---|---|
| Re. 34,985 | 6/1995 | Perning | 606/57 |
| 209,015 | 10/1878 | Bartram . | |
| 2,250,417 | 7/1941 | Ettinger . | |
| 2,333,033 | 10/1943 | Mraz | 606/57 |
| 2,371,519 | 3/1945 | Haynes | 606/54 |
| 2,391,537 | 12/1945 | Anderson . | |
| 3,581,592 | 6/1971 | Roehrs | 74/424.6 |
| 3,941,123 | 3/1976 | Volkov et al. . | |
| 4,033,340 | 7/1977 | Kalnberz . | |
| 4,100,919 | 7/1978 | Oganesyan et al. . | |
| 4,361,144 | 11/1982 | Slätis et al. . | |
| 4,483,334 | 11/1984 | Murray . | |
| 4,541,422 | 9/1985 | de Zbikowski . | |
| 4,615,338 | 10/1986 | Ilizarov et al. . | |
| 4,620,533 | 11/1986 | Mears . | |
| 4,662,365 | 5/1987 | Gotzen et al. . | |
| 4,765,651 | 8/1988 | Unger | 74/424.6 |
| 4,889,111 | 12/1989 | Ben-Dov . | |
| 5,062,844 | 11/1991 | Jamison et al. | 606/54 |
| 5,209,750 | 5/1993 | Stef | 606/54 |
| 5,219,349 | 6/1993 | Krag et al. | 606/53 |
| 5,242,445 | 9/1993 | Ashman | 608/53 |

FOREIGN PATENT DOCUMENTS

| | | |
|---|---|---|
| 1519673A1 | 11/1989 | U.S.S.R. . |
| 2077847 | 12/1981 | United Kingdom . |

OTHER PUBLICATIONS

Richards Medical Company, *Richards External Fixation Systems*, 1983, 8 pages.
Richards Medical Company, *The Ilizarov External Fixator General Technique Brochure*, 1988, cover and p. 17.
Aspen Publishers, "Basic Ilizarov Techniques," *Techniques in Orthopaedics®*, vol. 5, No. 4, Dec. 1990, cover and pp. 57–58.
Pfizer Hospital Products Group, Inc. (Howmedica), *Monticelli Spinelli® External Fixation System*, 1991, cover and pp. 1–28.
*Hex–Fix Surgical Technique* brochure, title page and pp. 1–7.

*Primary Examiner*—Michael Powell Buiz
*Assistant Examiner*—Mark S. Leonardo
*Attorney, Agent, or Firm*—Earl M. Douglas

[57] ABSTRACT

An external fixator for securing two or more bone elements. The external fixator includes an elongated bar; a first carriage for mounting on the bar and for securement to a first bone element; a second carriage for mounting on the bar and for securement to a second bone element; and a drive mechanism for driving the first and second carriages along the length of the bar independent of one another.

18 Claims, 3 Drawing Sheets

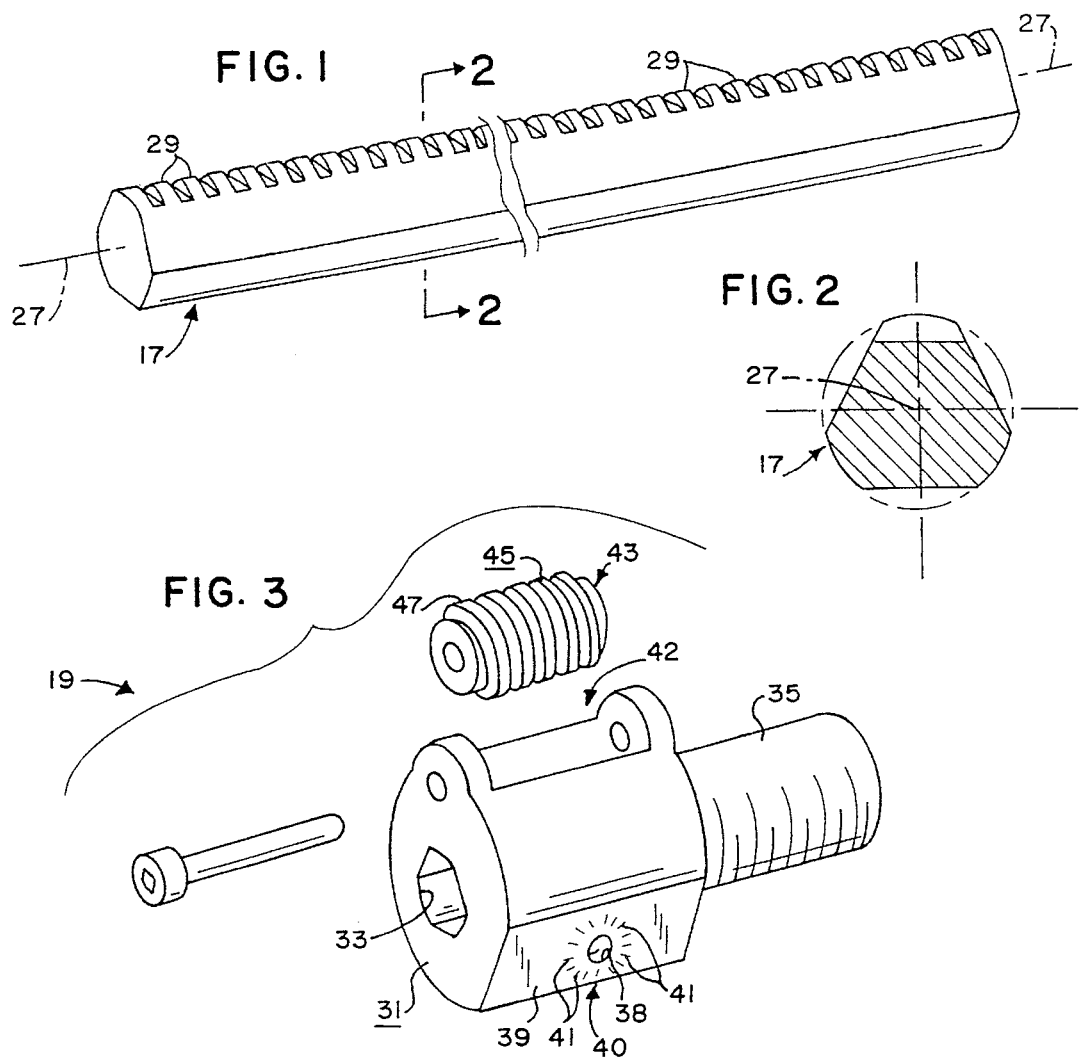

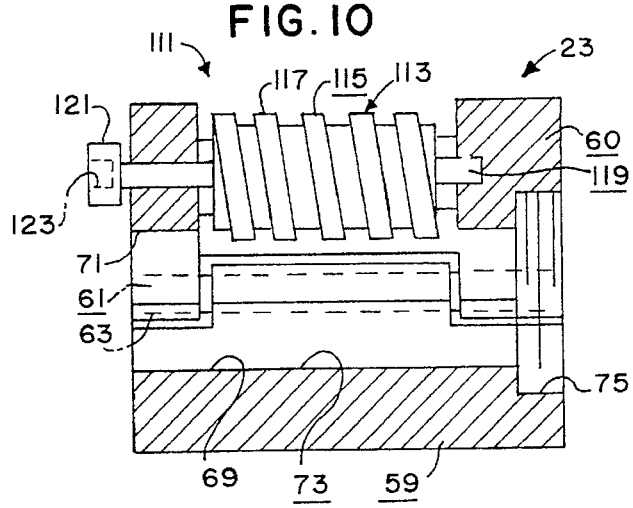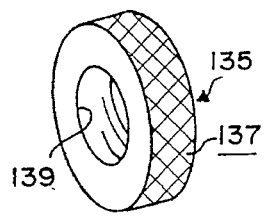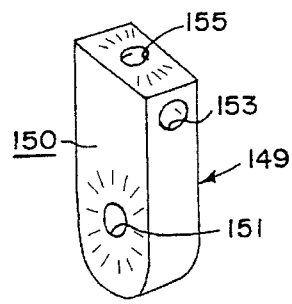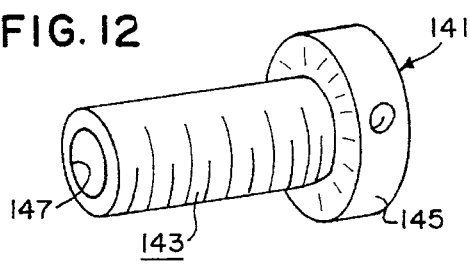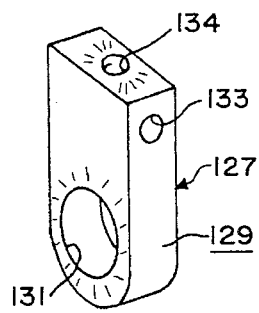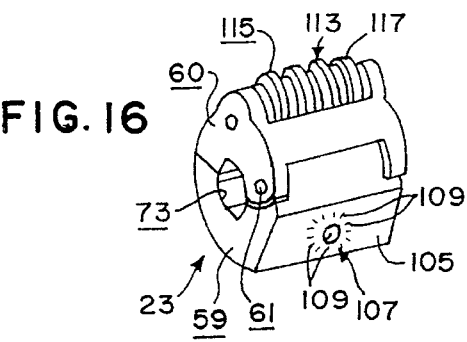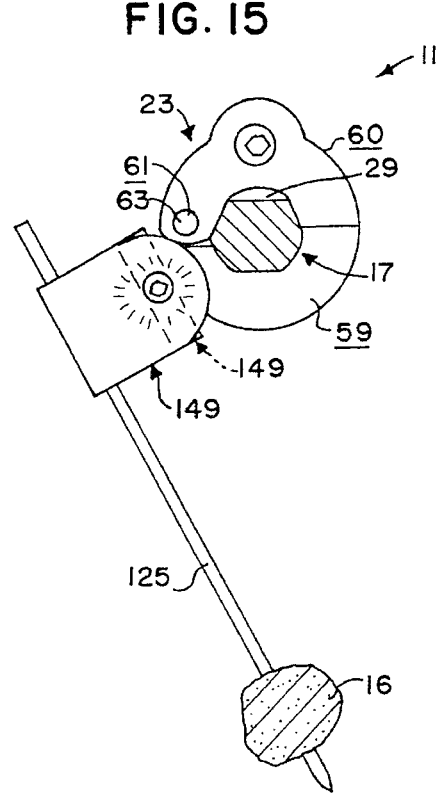

GEARED EXTERNAL FIXATOR

BACKGROUND OF THE INVENTION

1. Field of the Invention

The present invention relates, in general, to external fixators for securing one or more elements and, more specifically, to an improved geared bar and carriage combination for orthopedic external fixators that allows controlled, independent translation of two or more carriages.

2. Background Art

In the practice of medicine, it is sometimes desirable to treat certain injuries or conditions with an external frame that is attached to the boney skeleton with threaded and/or smooth pins and/or threaded and/or smooth and/or beaded wires. Such constructs are commonly referred to as orthopedic external fixators or external skeletal fixators. These external fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixator flames vary considerably in design and capabilities, and may include multiple or single bars or rods, and a plurality of clamps or connectors for adjustably securing the bars to pins or wires which are, in turn, joined to the boney skeleton. The pins or wires may extend completely through the boney skeleton and out each side of the limb or may extend through the boney skeleton and out only one side of the limb. Pins which extend completely through the boney skeleton and out both sides of the limb are commonly referred to as "transfixation pins." Pins which extend through the boney skeleton and out only one side of the limb are commonly referred to as "half pins." Materials for frames also vary, including metals, alloys, plastics, composites, and ceramics. External fixators vary in their ability to accommodate different spatial relations between each pin and bar, etc.

Mears, U.S. Pat. No. 4,620,533, issued Nov. 4, 1986, discloses an orthopedic external fixator including a plurality of transfixation pins 1, an elongated bar 2, and a plurality of pin-to-bar clamps 3 for adjustably attaching the pins 1 to the bar 2. The pin-to-bar clamps 3 including articulating balls 11 for holding the pins 1 and the bar 2 when thumbscrews or the like are tightened. In addition, Mears discloses a bar-to-bar clamp for allowing a second elongated bar 2A to be clamped relative to the bar 2.

In the course of treatment with external fixation, it is sometimes desirable or preferable to translate one or more bone fragments or to lengthen bones along an axis parallel to the axis of an external fixator bar. During such controlled translation or movement, it is deskable to maintain or control the other spatial relations of each fragment.

Ettinger, U.S. Pat. No. 2,250,417, issued Jul. 22, 1941, discloses an orthopedic external fixator for fracture reduction and retention including an elongated bar 1, a plurality of elongated threaded pins 36 for transfixing bone elements, a first connector or head 2 attached to one end of the bar 1 for joining a pair of the pins 36 to the bar 1, and a second connector or sleeve 5 slidably positioned on the bar 1 for connecting another pair of the pins 36 to the bar 1. A portion of the bar 1 is externally threaded and two nuts 3, 4 are screwably mounted on the bar 1, one on either end of the sleeve 5, so that proper rotation of the nuts 3, 4 will cause the sleeve 5 and associated pins 36 to move along the bar 1. The bar 1 has either a circular cross section with a longitudinal keyway for receiving a key 7 of the sleeve 5 (see FIG. 3), or a square cross section with rounded, threaded corners 9 (see FIG. 4) in which case the sleeve 5 is provided with a square bore to hold the sleeve 5 against rotation on the bar 1. The threads on the bar 1 and the threaded apertures through the nuts 3, 4 are arranged concentric with the longitudinal axis of the bar 1.

Anderson, U.S. Pat. No. 2,391,537, issued Dec. 25, 1945, discloses an orthopedic external fixator for fracture reduction including a pair of hollow robes 20, 21 telescopically joined together, a plurality of pins 15 for transfixing bone elements, a first fixation unit A slidably mounted on the tube 21 for connecting a pair of the transfixion pins 15 to the tube 21, and a second fixation unit B attached to the end of the tube 20 for connecting a pair of the transfixation pins 15 to the tube 20. The tube 20 is telescopically mounted within the tube 21. A threaded adjusting shaft 25 is mounted within the tubes 20, 21 and can be manually rotated by way of a wrench head 30 located at the outer end of the tube 21. Rotation of the shaft 25 causes a nut 32 nonrotatably located within the tube 20 to move longitudinally along the shaft 25. Coil springs 34 located within the tubes 20, 21 on either side of the nut 32 transfer longitudinal movement of the nut 32 to the tubes 20, 21 while permitting a certain desired yielding and eliminating any perfectly solid and hard contact.

Nothing in the known prior art discloses or suggests the present invention. More specifically, nothing in the known prior art discloses or suggests an external fixator including an elongated bar; a first carriage means mounted on the bar for securement to a first element; a second carriage means mounted on the bar for securement to a second element; and drive means for driving the first and second carriage means along the length of the bar independent of one another.

SUMMARY OF THE INVENTION

The present invention provides a geared external fixator for allowing controlled, independent translation of one or more elements.

The improved external fixator of the present invention includes, in general, an elongated bar; a first carriage means mounted on the bar for securement to a first element; a second carriage means mounted on the bar for securement to a second element; and drive means for driving the first and second carriage means along the length of the bar independent of one another.

One object of the present invention is to provide an external fixator which allows independent translation of two or more carriage means along the length of an external fixator bar.

Another object of the present invention is to provide an external fixator that prevents unwanted rotation of one or more carriage means around the transverse plane of a fixator bar while allowing translation of the carriage means along an axis parallel to the axis of the fixator bar.

Another object of the present invention is to provide an external fixator which allows translation of one or more carriage means along the fixator bar in controlled fashion.

Another object of the present invention is to provide an external fixator which allows multistation translation of pin clamp bodies.

Another object of the present invention is to provide an external fixator having a plurality of carriage means in which each carriage means may be translated along the bar independent of other carriage means or devices attached to the bar.

Another object of the present invention is to provide an external fixator which allows bone elements to be translated or lengthened along an axis parallel to the axis of the external fixator bar while maintaining and controlling the other spatial relations of each bone element.

Another object of the present invention is to provide an external fixator that allows for the independent motion for three or more carriage means.

Another object of the present invention is to provide an external fixator that allows a drive unit to be added to an existing non-driven spool.

Another object of the present invention is to provide an external fixator having an elongated bar, two or more carriage means movably mounted on the elongated bar, and drive means arranged eccentric to the longitudinal axis of the elongated bar for causing the carriage means to move along the elongated bar independent of one another.

BRIEF DESCRIPTION OF THE DRAWINGS

FIG. 1 is a perspective view of a geared bar of the external fixator of the present invention.

FIG. 2 is a somewhat diagrammatic sectional view substantially as taken on line 2—2 of FIG. 1 on a somewhat enlarged scale.

FIG. 3 is an exploded perspective view of a geared carriage means of the external fixator of the present invention.

FIG. 4 is an end elevational view of a geared carriage means of the external fixator of the present invention.

FIG. 5 is a sectional view substantially as taken on line 5—5 of FIG. 4.

FIG. 10 is a sectional view substantially as taken on line 10—10 of FIG. 8.

FIG. 11 is a perspective view of a spool ring for use with the external fixator of the present invention.

FIG. 12 is a perspective view of a spool member for use with the external fixator of the present invention.

FIG. 13 is a perspective view of an intermediate paddle for use with the external fixator of the present invention.

FIG. 14 is a perspective view of a single pin paddle for use with the external fixator of the present invention.

FIG. 15 is a somewhat diagrammatic sectional view of the external fixator of the present invention shown in combination with a human femur.

FIG. 16 is a perspective view of the carriage means of FIG. 8.

DESCRIPTION OF THE PREFERRED EMBODIMENT

Figure 6:
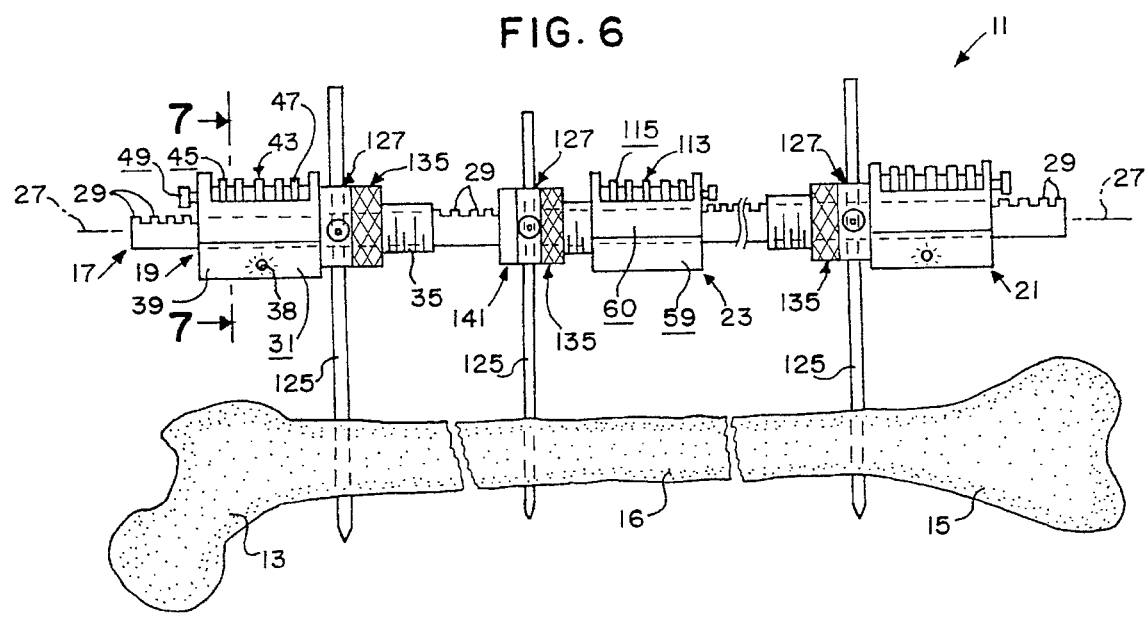
FIG. 6 is a somewhat diagrammatic view of the external fixator of the present invention shown in combination with a human femur.

A preferred embodiment of the external fixator of the present invention is shown diagrammatically in FIG. 6, and identified by the numeral 11. The external fixator 11 is used to secure one or more elements. For example, as diagrammatically shown in FIG. 6, the external fixator 11 can be used as an external skeletal fixator to secure or fix a first bone element 13 relative to a second bone element 15 and, if necessary, a third bone element 16 in the event of a break, fracture, etc.

As shown in FIG. 6, the external fixator 11 includes an elongated shaft, tube or bar 17; a first carriage means 19 for mounting on the bar 17 and for securement to the first bone element 13; a second carriage means 21 for mounting on the bar 17 and for securement to the second bone element 15; and drive means for driving or translating the first and second carriage means 19, 21 along the length of the bar 17 independent of one another. In addition, the external fixator 11 may include additional carriage means when necessary or desired. Thus, the external fixator 11 may include a third carriage means 23 for mounting on the bar 17 intermediate the first and second carriage means 19, 21 and for securement to one of the bone elements 13, 15, 16 (e.g., to the third bone element 16 as shown in FIG. 6). The drive means is associated with such additional carriage means for driving or translating such additional carriage means along the length of the bar 17 independent of one another and independent of the first and second carriage means 19, 21.

The bar 17 preferably consists of an elongated, rigid member having a longitudinal axis 27. The external fixator 11 preferably includes anti-rotation means for preventing undesired rotation of the carriage means 19, 21, 23 about the longitudinal axis 27 of the bar 17. More specifically, the bar 17 is preferably designed to coact with the carriage means 19, 21, 23, etc., in a manner that prevents rotation (within tolerances) of the carriage means 19, 21, 23, etc., around the longitudinal axis 27 of the bar 17. Thus, the bar 17 preferably has a nonrevolute cross section for non-rotatably mating with nonrevolute apertures in the carriage means 19, 21, 23, etc., to thereby form the anti-rotation means. Representative cross sections of the bar 17 include but are not limited to regular and irregular triangles, rectangles, pentagons, hexagons, septagons, octagons, nonagons, decagons, etc. Other possible cross sections include keyed circular cross sections and curved cross sections other than circular, such as, for example, elliptical. As shown generally in FIGS. 1 and 2, the bar 17 may have a generally polygonal cross section in which a somewhat irregular hexagonal shape is defined by three substantially flat sides joined by three generally curved sides.

The drive means preferably includes a bar gear member or means attached to and extending lengthwise of the bar 17. More specifically, regularly spaced positive or negative interdigitate members 29 such as teeth, holes, ridges, or grooves are provided along the length of the bar 17 for providing interdigitation with a corresponding mating mechanism on the carriage means 19, 21, 23, etc., to form the drive means as will hereinafter become apparent. These regularly spaced interdigitate members 29 allow the carriage means 19, 21, 23, etc., to be held in place or moved along the bar 17 by means of appropriate gears, belts, chains, beaded cables, etc., as will hereinafter be described. As shown clearly in FIGS. 1 and 6, the interdigitate members 29 may consist of a plurality of alternating rack gear teeth and grooves machined or otherwise formed in one of the generally curved sides of the bar 17. The interdigitate members 29 preferably extend transverse to the longitudinal axis 27 of the bar 17 and are preferably arranged eccentric to the longitudinal axis 27 of the bar 17 as clearly shown in FIG. 2.

The bar 17 may be manufactured in various sizes, out of various materials, and in various methods as will now be apparent to those skilled in the art. Thus, for example, the bar 17 may be formed out of an elongated rod or cylinder of stainless steel or the like three flat sides milled or otherwise formed therein, as illustrated by the imaginary lines shown in FIG. 2, leaving three curved sides, and with the interdigitate members 29 cut or otherwise machined in one of the curved sides. Further, the bar 17 may be cannulated or tubular as will now be apparent to those skilled in the art.

A first embodiment of the carriage means is shown in FIGS. 3–7 and illustrated by the first and second carriage means 19, 21 and described herebelow with respect to the first carriage means 19. A second embodiment of the carriage means is shown in FIGS. 6, 8–10 and 15 and illustrated by and described herebelow with respect to the third carriage means 23.

Figure 7:
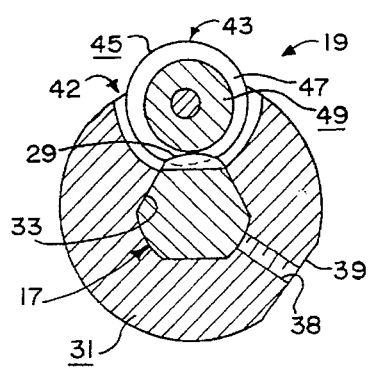
FIG. 7 is a sectional view substantially as taken on line 7—7 of FIG. 6 with portions omitted for clarity.

Thus, the first embodiment of the carriage means as represented by the first carriage means 19 preferably includes a body member 31 having an aperture 33 for receiving the bar 17. The aperture 33 is designed to coact with the bar 17 in a manner that prevents rotation (within tolerances) of the first carriage means 19 around the longitudinal axis 27 of the bar 17. Thus, the aperture 33 preferably has a nonrevolute cross-sectional shape for non-rotatably mating with the nonrevolute cross section of the bar 17. The cross-sectional shape of the aperture 33 is complementary with the cross section of the bar 17 so that rotation (within tolerances) of the first carriage means 19 around the longitudinal axis 27 of the bar 17 is prevented. Representative cross-sectional shapes of the aperture 33 include but are not limited to regular and irregular triangles, rectangles, pentagons, hexagons, septagons, octagons, nonagons, decagons, etc. Other possible cross-sectional shapes include keyed circular cross-sectional shapes and curved cross-sectional shapes other than circular, such as, for example, elliptical. As shown in FIGS. 4 and 7, the aperture 33 may have a generally polygonal cross-sectional shape in which a somewhat irregular hexagonal shape is defined by three substantially flat sides joined by three generally curved sides.

The body member 31 is preferably designed so as to allow various connector constructs to be attached thereto. Such connector constructs include, but are not limited to pin clamps, fixator bars, hinge and virtual hinge mechanisms, and translation mechanisms. Thus, one end of the body member 31 preferably includes an externally threaded cylindrical boss or spool 35 for allowing typical connector constructs to be attached thereto in a manner as will hereinafter be described. The aperture 33 extends through the spool 35 as clearly shown in FIG. 5. In addition, the body member 31 may have a threaded aperture 38 in one side thereof for allowing typical connector constructs to be attached thereto in a manner as will hereinafter be described. A flat 39 may be milled across one face of the body member 31 adjacent the threaded aperture 38 for allowing such connector constructs to make secure contact with the body member 31. In addition, grip enhancing means 40 is preferably provided on the flat 39 adjacent the threaded aperture 38 for enhancing the grip between the body member 31 and the connector constructs, etc. The grip enhancing means 40 preferably consist of a plurality of raised or indented splines or teeth 41 formed in the surface of the flat 39 and radiating from the center of the threaded aperture 38.

The body member 31 preferably has an opening 42 through one side communicating with the aperture 33 for reasons which will hereinafter become apparent.

The body member 31 may be manufactured in various sizes, out of various materials, and in various methods as will now be apparent to those skilled in the art. Thus, for example, the body member 31 and spool 35 may be machined as a one-piece, integral unit out of stainless steel or the like sized so as to coact with existing pin clamps and the like.

The first carriage means 19 preferably includes a carriage gear member or means 43 for drivably engaging the interdigitate members 29 of the bar 17 so that movement of the gear means 43 and the interdigitate members 29 relative to one another will cause the first carriage means 19 to move lengthwise of the bar 17 independent of any other carriage means mounted on the bar 17. More specifically, the gear means 43 is designed and attached to the body member 31 for drivably engaging the bar 17 when the bar 17 is received within the aperture 33 of the body member 31 to allow controlled translation of the first carriage means 19 along the length of the bar 17. The gear means 43 preferably includes a worm or wheel member 45 rotatably mounted within the opening 42 in the body member 31. The wheel member 45 preferably has regularly spaced interdigitate members 47 such as teeth, holes, ridges, or grooves that provide interdigitation with the corresponding interdigitate members 29 on the bar 17 to form the drive means as will hereinafter be described. These regularly spaced positive or negative interdigitate members 47 allow the first carriage means 19 to be held in place or moved along the bar 17 by means of appropriate gears, belts, chains, beaded cables, etc., as will hereinafter become apparent. As shown generally in FIGS. 3 and 5, the interdigitate members 47 may consist of alternating worm gear teeth and spaces machined or otherwise formed in the outer surface of the wheel member 45 for engaging the corresponding interdigitate members 29 on the bar 17 so that rotation of the wheel member 45 will cause controlled translation of the first carriage means 19 along the length of the bar 17 as will now be apparent to those skilled in the art. The wheel member 45 may be rotated by hand, tool, motor (electric, air, hydraulic, or spring), etc., as will now be apparent to those skilled in the art. As shown generally in FIGS. 3 and 5, the wheel member 45 may be rotatably attached to the body member 31 by way of an axle 49 fixedly attached to the wheel member 45 and rotatably attached to the body member 31, and the means for rotating the wheel member 45 may include a head member 51 attached to one end of the axle 49 for being engaged and rotated by a tool. Thus, for example, the head member 51 may have a socket 53 therein for being engaged and rotated by a standard Allen wrench or the like. The gear means 43, including the wheel member 45 and axle 49, is thus mounted eccentric to the longitudinal axis of the aperture 33 and the longitudinal axis 27 of the bar 17 when the bar 17 is positioned within the aperture 33.

The second carriage means 21 is preferably substantially similar to the first carriage means 19 and the above description of the first carriage means 19 should be consulted for a full understanding of the construction and operation of the second carriage means 21.

The second embodiment of the carriage means as represented by the third carriage means 23 and shown in FIGS. 6, 7–10 and 15 is preferably especially designed as an openable carriage means for being placed onto the bar 17 at a point intermediate the opposite ends of the bar 17. For example, during surgical treatment of the bone elements 13, 15, 16 shown in FIG. 6 with the external fixator 11 of the present invention, it may become desirable after the first and second carriage means 19, 21 have been placed on the bar 17 and affixed to the first and second bone elements 13, 15, respectively, to place the third carriage means 23 between the previously affixed first and second carriage means 19, 21. Thus, the third carriage means 23 is especially designed so that it can be placed on the bar 17 between the first and second carriage means 19, 21 without requiring the first and/or second means 19, 21 to be first removed from the bar 17, or can be coupled to an existing spool mounted on the bar 17 to allow that existing spool to be driven or motorized.

Accordingly, as shown in FIGS. 8–10 and 15, the third carriage means 23 preferably includes a first body member 59 for extending around a portion of the bar 17, a second body member 60 for extending around another portion of the bar 17, and joining means 61 for joining the first and second body members 59, 60 to one another around the bar 17 and for allowing the first and second members 59, 60 thereof to be separated from one another so that the third carriage means 23 can be placed on or removed from the bar 17 at locations intermediate the opposite ends of the bar 17.

Figure 8:
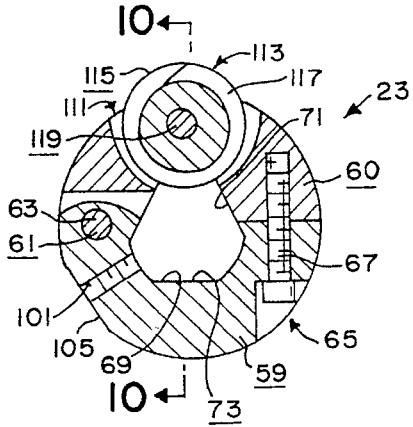
FIG. 8 is a sectional view substantially similar to FIG. 7 but showing an alternate embodiment of a geared carriage means of the external fixator of the present invention.
Figure 9:
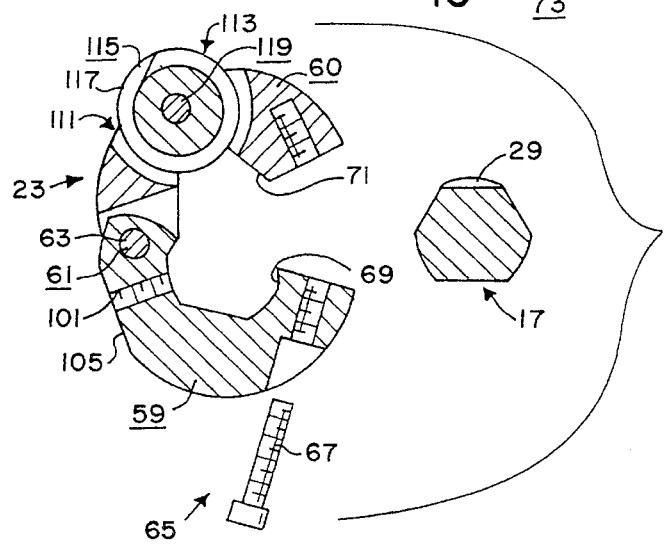
FIG. 9 is an exploded view of the carriage means of FIG. 8, shown in combination with a geared bar of the external fixator of the present invention.

The joining means 61 preferably includes hinge means 63 for hingeably attaching the first and second body members 59, 60 to one another and for allowing the first and second body members 59, 60 to be moved between a closed position as shown in FIGS. 8 and 10, and an open position as shown in FIG. 9.

The third carriage means 23 preferably includes lock means 65 for selectively locking the first and second body members 59, 60 in the closed position. The lock means 65 may consist simply of one or more screw members 67 for screwing the first and second body members 59, 60 to one another in the closed position.

The first body member 59 preferably has a groove 69 thereacross and the second body member 60 preferably has a groove 71 thereacross that coact to form an aperture 73 for receiving the bar 17 when the first and second body members 59, 60 are in the closed position shown in FIGS. 8, 10 and 15. The aperture 73 is designed to coact with the bar 17 in a manner that prevents rotation (within tolerances) of the third carriage means 23 around the longitudinal axis 27 of the bar 17. Thus, the aperture 73 preferably has a nonrevolute cross-sectional shape for non-rotatably mating with the nonrevolute cross section of the bar 17. The cross-sectional shape of the aperture 73 may be identical to the cross-sectional shape of the aperture 33 and is complementary with the cross section of the bar 17 so that rotation (within tolerances) of the first carriage means 19 around the longitudinal axis 27 of the bar 17 is prevented. Thus, representative cross-sectional shapes of the aperture 73 include but are not limited to regular and irregular triangles, rectangles, pentagons, hexagons, septagons, octagons, nonagons, decagons, etc. Other possible cross-sectional shapes include keyed circular cross-sectional shapes and curved cross-sectional shapes other than circular, such as, for example, elliptical. As shown generally in FIGS. 8 and 15, the aperture 73 may have a generally polygonal cross-sectional shape in which a somewhat irregular hexagonal shape is defined by three substantially flat sides joined by three generally curved sides. The aperture 73 thus may have the same cross sectional shape and area as the aperture 33 of the body member 31.

The body members 59, 60 are preferably designed so as to allow various connector constructs to be attached thereto. Such connector constructs include, but are not limited to pin clamps, fixator bars, hinge and virtual hinge mechanisms, and translation mechanisms. For example, one end of each body member 59, 60 is designed so as to form an internally threaded shoulder 75 at one end of the aperture 73 when the body members 59, 60 are in the closed position for allowing typical connector constructs to be attached thereto in a manner as will hereinafter be described. In addition, the body member 59 may have a threaded aperture 101 in one side thereof for allowing typical connector constructs to be attached thereto in a manner as will hereinafter be described. A flat 105 may be milled across one face of the body member 59 adjacent the aperture 101 for allowing such connector constructs to make secure contact with the body member 59. In addition, grip enhancing means 107 is preferably provided on the flat 105 adjacent the aperture 101 (see FIG. 16) for enhancing the grip between the body member 59 and the connector constructs, etc. The grip enhancing means 107 preferably consist of a plurality of raised or indented splines or teeth 109 formed in the surface of the flat 105 and radiating from the center of the aperture 101.

One of the body members 59, 60 (e.g., the body member 60) preferably has a opening 111 through one side communicating with the aperture 73 for reasons which will hereinafter become apparent.

The body members 59, 60 may be manufactured in various sizes, out of various materials, and in various methods as will now be apparent to those skilled in the art. Thus, for example, the body members 59, 60 may be machined out of stainless steel or the like sized so as to coact with existing pin clamps and the like.

The third carriage means 23 preferably includes a carriage gear member or means 113 for drivably engaging the interdigitate members 29 of the bar 17 so that movement of the gear means 113 and the interdigitate members 29 relative to one another will cause the third carriage means 23 to move lengthwise of the bar 17 independent of any other carriage means mounted on the bar 17. More specifically, the gear means 113 is designed and attached to the body member 60 for drivably engaging the bar 17 when the bar 17 is received within the aperture 73 of the body members 59, 60 to allow controlled translation of the third carriage means 23 along the length of the bar 17. The gear means 113 preferably includes a worm or wheel member 115 rotatably mounted within the opening 111 in the body member 60. The wheel member 115 preferably has regularly spaced interdigitate members 117 such as teeth, holes, ridges, or grooves that provide interdigitation with the corresponding interdigitate members 29 on the bar 17 to form the drive means as will hereinafter be described. These regularly spaced positive or negative interdigitate members 117 allow the third carriage means 23 to be held in place or moved along the bar 17 by means of appropriate gears, belts, chains, beaded cables, etc., as will hereinafter become apparent. As shown generally in FIG. 10, the interdigitate members 117 may consist of alternating worm gear teeth and spaces machined or otherwise formed in the outer surface of the wheel member 115 for engaging the corresponding interdigitate members 29 on the bar 17 so that rotation of the wheel member 115 will cause controlled translation of the third carriage means 23 along the length of the bar 17 as will now be apparent to those skilled in the art. The wheel member 115 may be rotated by hand, tool, motor (electric, air, hydraulic, or spring), etc., as will now be apparent to those skilled in the art. As shown generally in FIG. 10, the wheel member 115 may be rotatably attached to the body member 60 by way of an axle 119 fixedly attached to the wheel member 115 and rotatably attached to the body member 60, and the means for rotating the wheel member 115 may include a head member 121 attached to one end of the axle 119 for being engaged and rotated by a tool. Thus, for example, the head member 121 may have a socket 123 therein for being engaged and rotated by a standard Allen wrench or the like. The gear means 113, including the wheel member 115 and axle 119, is thus mounted eccentric to the longitudinal axis of the aperture 73 and the longitudinal axis 27 of the bar 17 when the bar 17 is positioned within the aperture 73.

As clearly indicated in FIG. 9, the third carriage means 23 can be placed onto the bar 17 at a point intermediate the opposite ends of the bar 17 by merely unscrewing the screw members 67, then moving the first and second body members 59, 60 to the open position in a clamshell-like fashion, then closing the first and second body members 59, 60 over the bar 17, and then locking the first and second body members 59, 60 over the bar 17 in the closed position by screwing in the screw members 67. The third carriage means 23 can be removed from the bar 17 at a point intermediate the opposite ends of the bar 17 by merely reversing the above steps as will now be apparent to those skilled in the art.

It should be noted that the first and second carriage means 19, 21 can also be constructed as clam-shell constructs similar to the above description of the third carriage means 23 and the above description of the third carriage means 23 should be consulted for a full understanding of such alternative construction and operation. Further, the third carriage means 23 can be constructed as a fixed or non-opening construct similar to the above description of the first carriage means 19 and the above description of the first carriage means 19 should be consulted for a full understanding of such alternative construction and operation.

The initial steps in the method of using the external fixator 11 for external boney fixation is similar to prior external fixators as will now be apparent to those skilled in the art. For example, to stabilize the broken femur shown in FIG. 6, standard bone pins 125, such as standard half pins, transfixation pins, or the like, are inserted or drilled into the bone fragments and the distal ends of each pin 125 are, in turn, connected to one of the carriage means 19, 21, 23 via standard connector constructs. For example, a standard single pin paddle 127 as shown in FIGS. 6 and 15 can be used to connect a pin 125 to the first carriage means 19. More specifically, the single pin paddle 127 may include a plate-like body 129 having an aperture 131 extending therethrough sized so as to fit onto the spool 35 of the body member 31 of the first carriage means 19, etc. The body 129 may have a bore 133 therethrough for allowing a pin 125 to pass therethrough, and may have a threaded aperture 134 for allowing a set screw or the like to fixedly secure the pin 125 within the bore 133, etc. as will now be apparent to those skilled in the art. A standard spool nut or ring 135 as shown in FIGS. 6 and 11 can be used to secure the single pin paddle 127 to the first carriage means 19. Thus, the spool ring 135 may include a body 137 having a threaded aperture 139 for being screwed onto the threaded spool 35 of the first carriage means 19 so as to clamp the pin paddle 127 against one side of the body member 31 as will now be apparent to those skilled in the art. Similar connector constructs may be used to connect a pin 125 to the second carriage means 21 as shown in FIG. 6.

Such connector constructs may include a typical spool component 141 as shown in FIGS. 6 and 12 for allowing a pin paddle 127 or the like to the third carriage means 23. Such a typical spool component 141 is shown in detail in FIG. 12, and commonly includes a cylindrical body 143 having external threads about which the internally threaded shoulder 75 of the third carriage means 23 can be closed by closing the first and second body members 59, 60 thereover, having a flange 145 at one end, and having a longitudinal aperture or bore 147 extending therethrough for slidably receiving the bar 17. The aperture 131 of a single pin paddle 127 can be passed over the cylindrical body 143 of the spool component 141 and the pin paddle 127 can then be secured to the spool component 141 with the use of a spool rings 135 as will now be apparent to those skilled in the art.

In addition, the connector constructs may include an intermediate paddle 149 as shown in FIG. 13, or the like, with a plate-like body 150 for being secured to the threaded aperture 38 of the first carriage means 19 or the threaded aperture 101 of the third carriage means 23, etc., using a bolt or the like through an aperture 151 therethrough as will now be apparent to those skilled in the art. The body 150 may have a bore 153 therethrough for allowing a pin 125 to pass therethrough, and may have a threaded aperture 155 for allowing a set screw or the like to fixedly secure the pin 125 within the bore 153, etc. as will now be apparent to those skilled in the art. On the other hand, the connector constructs may include two intermediate paddles 149 with the pin 125 extending through the bore 153 of a first one of the paddles 149 and secured thereto by way of a set screw extending into the threaded aperture 155, with the second one of the paddles 149 secured to the third carriage means 23 by means of a bolt extending through the aperture 151 of that paddle 149 into the threaded aperture 101 of the third carriage means 23, and with the first one of the paddles 149 secured to the second one of the paddles 149 by way of a bolt extending through the aperture 151 of the first one of the paddles 149 into the threaded aperture 155 in the second one of the paddles 149 as illustrated in FIG. 15 and as will now be apparent to those skilled in the art. With the first carriage means 19 mounted on the bar 17, rotation of the axle 49 thereof will cause the first carriage means 19 and its associated connector constructs, pin 125, bone element 13 and the like to be controllably translated along the longitudinal axis 27 of the bar 17 independently of the second and third carriage means 21, 23. Likewise, with the second carriage means 21 mounted on the bar 17, rotation of the axle 49 thereof will cause the second carriage means 21 and its associated connector constructs, pin 125, bone element 15 and the like to be controllably translated along the longitudinal axis 27 of the bar 17 independently of the first and third carriage means 19, 23. Further, with the third carriage means 23 mounted on the bar 17, rotation of the axle 119 thereof will cause the third carriage means 23 and its associated connector constructs, pin 125, bone element 16 and the like to be controllably translated along the longitudinal axis 27 of the bar 17 independently of the first and second carriage means 19, 21. It should be noted that the actual number and type of pins, connector constructs, carriage means, etc., can vary depending on the bone elements being secured and the surgeon's desires, etc., as will now be apparent to those skilled in the art. One benefit of the external fixator 11 of the present invention is that each carriage means, and its associated connectors, pins and bone elements, can be further translated independently of all other carriage means, etc., either during the initial surgery or periodically after the initial surgery over a period of time, to produce the desired result. Further, another benefit of the external fixator 11 of the present invention is that additional carriage means and associated structure can be applied between or intermediate other carriage means and associated structure anytime after the initial stabilization. Thus, for example, the third carriage means 23 shown in FIGS. 8–10 and 15, can be placed around the bar 17 intermediate the first and second carnage means 19, 21 and after the first and second carriage means 19, 21 have been attached to the bar 17.

As thus constructed and operated, the present invention provides an external fixator that prevents unwanted rotation around the transverse plane of the fixator bar while allowing translation along an axis parallel to the axis of the fixator bar. Furthermore, not only allowing translation along the bar, the carriage means allows translation in controlled fashion along the external fixation bar. Used in conjunction with complementary geared external fixator bar, several carriage means may be applied on the fixator bar and independent translation along the bar may be accomplished by each carriage means.

Although the present invention has been described and illustrated with respect to preferred embodiments and preferred uses therefor, it is not to be so limited since modifications and changes can be made therein which are within the full intended scope of the invention.

We claim:

1. An external fixator for securing first and second bone elements during a healing process; said external fixator comprising:
   (a) an elongated bar;
   (b) a first carriage for mounting on said bar and for securement to the first bone element;
   (c) a second carriage for mounting on said bar and for securement to the second bone element;
   (d) a first drive mechanism associated with said first carriage for driving said first carriage along the length of said bar; and
   (e) a second drive mechanism associated with said second carriage for driving said second carriage along the length of said bar independent of said first carriage;
   wherein the fixator controls the relative alignment of said first and second bone segments during the healing processes.

2. The external fixator of claim 1 wherein said bar has a longitudinal axis; and said fixator further includes an anti-rotation mechanism for preventing undesired rotation of said first and second carriages about said longitudinal axis of said bar.

3. The external fixator of claim 1 in which said drive mechanism includes bar gears attached to and extending along said bar; and wherein at least one of said first and second carriages includes carriage gears for drivably engaging said bar gears so that movement of said bar gears and said carriage gears relative to one another will cause said carriage associated with said carriage gears to move along said bar independent of the other carriage.

4. The external fixator of claim 2 wherein said anti-rotation mechanism includes:
   (a) a first aperture that extends through said first carriage and a second aperture that extends through said second carriage, whereby said first and second apertures have noncircular cross sections; and
   (b) a cross section of said bar that is complementary with the cross sections of said noncircular first and second apertures.

5. The external fixator of claim 1 further comprising an openable carriage having a first member for extending around a first portion of said bar, a second member for extending around a second portion of said bar, and a joint for joining said first and second members to one another and allowing said first and second members thereof to be separated from one another so that said openable carriage can be repeatedly secured to or removed from said bar at locations intermediate the opposite ends of said bar.

6. The device of claim 5 wherein said carriage includes a lock for securing said carriage around said bar while allowing said carriage to move along said bar.

7. The external fixator of claim 1 further comprising an openable carriage having a first member for extending around a portion of said bar, a second member for extending around another portion of said bar, and a hinge joining said first and second members to one another and allowing said first and second members thereof to be separated from one another so that said openable carriage can be placed on or removed from said bar at locations intermediate the opposite ends of said bar.

8. An external fixator for securing and independently translating first, second and third bone elements; said external fixator comprising:
   (a) an elongated bar having a first end and a second end;
   (b) a first carriage for mounting on said bar and for securement to the first bone element;
   (c) a second carriage for mounting on said bar and for securement to the second bone element;
   (d) a third carriage for mounting on said bar intermediate said first and second carriages and for securement to the third bone element; and
   (e) a driver associated with at least one of said first, second and third carriages for driving said associated carriage along said bar independent of the carriages not associated with said driver;
   said third carriage including a first member for extending around a portion of said bar, a second member for extending around another portion of said bar, and a joint for joining said first and second members to one another around said bar and for allowing said first and second members thereof to be separated from one another so that said third carriage can be repeatedly placed on or removed from said bar at locations intermediate said first and second carriage.

9. The external fixator of claim 8 in which said driver includes bar gears attached to and extending along said bar; and wherein at least one of said first, second, and third carriages includes a carriage gears for drivably engaging said bar gears so that movement of said carriage gears and said bar gears relative to one another will cause said carriage associated with said carriage gears to move along said bar independent of the other carriages.

10. The external fixator of claim 9 further comprising an anti-rotation mechanism for preventing undesired rotation of said carriage about said bar.

11. The external fixator of claim 10 wherein said anti-rotation mechanism includes:
   (a) a first aperture that extends through said first carriage, a second aperture that extends through said second carriage and a third aperture that extends through said third carriage, whereby said first, second and third apertures have noncircular cross sections; and
   (b) a cross section of said bar that is complementary with the cross sections of said noncircular first, second and third apertures.

12. A carriage for an orthopedic external fixator including an elongated bar having a first end and a second end, said carriage comprising:
   (a) a body member for engaging a portion of said bar;
   (b) a lock movable between an open position and a closed position for allowing said body member to be placed on or removed from said bar at locations intermediate said first and second ends of said bar when in the open position and for locking said body member to said bar when in the closed position while allowing said body member to move along said bar.

13. The carriage of claim 12 further comprising a drive mechanism that engages said bar when said body member is locked to said bar, whereby said drive mechanism causes said carriage to move along said bar.

14. The carriage of claim 13 in which said drive mechanism is adapted to be arranged eccentric to a longitudinal axis of said bar.

15. The carriage of claim 12 wherein said lock secures said body member to said bar while allowing said body member to move along said bar.

16. The carriage of claim 12 wherein said a body member includes a first segment and a second segment interconnected with a hinge.

17. The carriage of claim 13 further comprising an anti-rotation mechanism for coacting with said bar for preventing undesired rotation of said carriage about said bar.

18. An external fixator for securing first and second elements; said external fixator comprising:

(a) an elongated bar having first and second ends, having a longitudinal axis extending between said first and second ends, and having a plurality of gear teeth located between said first and second ends;

(b) a carriage for mounting on said bar and for securement to one of said first and second elements;

(c) a drive mechanism attached to said carriage for engaging said gear teeth of said bar and for causing said carriage to move back and forth along said bar;

said gear teeth and said drive mechanism being arranged eccentric of said longitudinal axis of said bar.

\* \* \* \* \*